United States Patent [19]

Ehrlich et al.

[11] Patent Number: 5,662,927

[45] Date of Patent: Sep. 2, 1997

[54] METHOD OF HORMONAL CONTRACEPTION

[76] Inventors: Marika Ehrlich, Bahnhofstr. 1, D55234 Framersheim; Herbert Kuhl, Hotzelstr. 18, D63741 Aschaffenburg, both of Germany

[21] Appl. No.: 360,297

[22] Filed: Dec. 21, 1994

[30] Foreign Application Priority Data

Dec. 24, 1993 [DE] Germany .................. 43 44 405.9

[51] Int. Cl.$^6$ ................................... A61F 13/00
[52] U.S. Cl. .................. 424/449; 424/464; 514/170; 514/843
[58] Field of Search .................. 424/449, 464; 514/170, 843

[56] References Cited

U.S. PATENT DOCUMENTS

| | | |
|---|---|---|
| 3,733,407 | 5/1973 | Segre ........................ 514/170 |
| 4,921,843 | 5/1990 | Pasquale ................. 514/170 |
| 5,280,023 | 1/1994 | Ehrlich et al. ........... 514/177 |

FOREIGN PATENT DOCUMENTS

| | | |
|---|---|---|
| 41 04 385 | 8/1992 | Germany . |
| 43 08 406 | 6/1994 | Germany . |

OTHER PUBLICATIONS

Ehrlich et al., *Chemical Abstracts*, vol. 120, Apr. 4, 1994, #173484.
Ehrlich et al., *Chemical Abstracts*, vol. 122, 1993, #114,969.

*Primary Examiner*—D. Gabrielle Phelan
*Attorney, Agent, or Firm*—Hill, Steadman & Simpson

[57] ABSTRACT

A method for hormonal contraception having a first hormonal component and a second hormonal component packaged separately in a packing unit and intended for short-term sequential administration, each of the hormonal components being composed of a plurality of daily hormone units separately packaged and individually removable in the packing unit. The first hormonal component contains almost exclusively an estrogen preparation as an active hormonal ingredient, effecting a disturbance of the follicle stimulation. The second hormonal component contains, in combination, an estrogen preparation and a progestogen preparation in a therapeutic amount sufficient for ovulation inhibition. The total number of daily hormone units is equal to the total number of days of the desired cycle, with the first hormonal component including 5 or 14 daily units and the second hormonal component including 23 or 14 daily units. The plurality of daily units of the first hormonal component is lower than the plurality of daily units of the second hormonal component, characterized by such an arrangement of the daily units in the packaging unit that the daily units of the second hormonal component are taken first and the daily units of the first hormonal component are taken thereafter. The daily units of the second hormonal component do not contain the combination of biologically produced estrogen and synthetic estrogen.

24 Claims, No Drawings

METHOD OF HORMONAL CONTRACEPTION

BACKGROUND OF THE INVENTION

The present invention relates to a method of hormonal contraception. More particularly, the present invention relates to two hormonal components separately packaged in a packaging unit and intended for short-term sequential administration. The hormonal components are respectively composed of a plurality of daily hormone units packaged separately and individually removable in the packaging unit. The first hormonal component contains an estrogen preparation as an active hormonal ingredient that impairs follicle stimulation. The second hormonal component contains an estrogen preparation and a progestogen preparation in a dose at least adequate for inhibiting ovulation in combination, and the total number of daily hormone units is equal to the total number of days of the desired cycle. The first hormonal component comprises 5 or 14 daily units and the second hormonal component comprises 23 or 14 daily units. The plurality of daily units of the first hormonal component is lower than the plurality of daily units of the second hormonal component.

German Letters Patent 41 04 385 discloses a method of inhibiting ovulation as well as a method for hormonal contraception of the above-described type, whereby the daily units of the first hormonal component are first administered and those of the second hormonal component are administered thereafter in daily succession, preferably for hormonal contraception within the desired cycle, on which the first daily unit of the first hormonal component of the next cycle is repeated upon exclusion of breaks in administration.

SUMMARY OF THE INVENTION

An advantage of the present invention is that it provides continuous administration of the estrogen component, i.e., of the daily units of the first hormonal component. Heretofore, the method of ovulation inhibition has involved the administration-free interval of 6 or 7 days. It has been shown, however, that follicle stimulation is disturbed, but ovulation is not reliably prevented given initial employment of the method whereby the first hormonal component is given in a beneficially low dosage of the daily units in order to minimize the health risk. This low contraception reliability in the first administration cycle compared to the following administration cycles is based on the fact that the new follicle stimulation is already in the last part of the luteal phase of the preceding ovulation cycle when the endogenous gestradiol, the endogenous estradiol and the endogenous progesterone decrease.

Given the initial employment of a conventional ovulation inhibitor that provides an administration-free interval, whereby administration of the tablets normally begins approximately on the fifth day after the beginning of menstruation, the contraceptive reliability can be enhanced if the conventional ovulation inhibitor is administered on the first day of menstruation (Martindale 1993, p. 1177). Due to the application of the estrogen/progestogen combination at this early point in time, ovulation is thereby reliably prevented, whereby it is accepted that the first administration cycle is shortened, i.e., a cycle length of approximately 24 days up to the beginning of the next withdrawal bleeding. For the same reason, it has already been recommended with traditional preparations to either shorten the administration-free interval or entirely omit it in the first administration cycle, when switching from a highly dosed ovulation inhibitor to a lowly dosed ovulation inhibitor (Martindale 1993, p. 1177).

Since the follicle stimulation in a normal ovulatory cycle already begins in the last third of the luteal phase (preceding menstruation), a reliable contraception cannot be reliably assured, given initial administration of the ovulation-inhibition method of the type when daily units of the first hormonal component, that are dosed especially low, are started on the first day of menstruation. This is because the first administration cycle up to the following withdrawal bleeding would be lengthened to approximately 30 days.

German Letters Patent 43 08 406 (not enjoying prior publication) already discloses a method of ovulation-inhibition in the form of a combination preparation for contraception, whereby at least one hormonal component containing both estrogen as well as progestogen is provided, whereby the daily units contain both a biologically produced estrogen as well as a synthetic estrogen. The present invention is not directed to such preparations.

An advantage provided by the present invention is to improve the ovulation-inhibiting means as well as the method of the type to achieve high contraceptive reliability even when administration entails employing daily units of the first hormonal component with an extremely low dose.

To this end, the present invention provides an arrangement of the daily units in the packaging unit whereby the daily units of the second hormonal component are taken first and the daily units of the first hormonal component are taken thereafter. The daily units of the second hormonal component do not contain the combination of a biologically produced estrogen and a synthetic estrogen.

It can thereby be provided that the total number of daily units is continuously numbered according to administration days over the entire desired cycle, beginning with the allocation of the first daily unit of the second hormonal component on the first administration day.

In an embodiment, the invention provides a fixed numbering of the daily units.

In another embodiment, the invention provides a variable numbering of the daily units in such a way that the first administration day can be optionally assigned to the first daily unit of the first or of the second hormonal component.

In yet another embodiment, the invention provides that at least one of the hormonal components is suitable for oral administration;

In another embodiment, the invention provides that at least one of the hormonal components is suitable for transdermal administration.

In another embodiment, the invention provides that at least some of the daily units of at least one of the hormonal components is combined to form a sustained release unit.

In still another embodiment, the invention provides that at least two pairs of first and second hormonal components are packaged separately in a packaging unit.

In an embodiment, the invention provides that at least one sustained release unit overlaps at least two hormonal component pairs.

Furthermore; another embodiment of the present invention provides that the daily units of the second hormone component or components contain an estrogen content that incrementally increases.

DESCRIPTION OF THE PREFERRED EMBODIMENTS

Pursuant to the present invention, a method is provided which employs the administration of the first daily unit of the second hormonal component on the first day of menstruation when initially administered. All further daily units of the second hormonal component are taken thereafter without an administration-free interval. All daily units of the first hormonal component are taken thereafter without an administration-free interval. Finally, the administration of the first daily unit of the second hormonal component of the following cycle follows thereafter without an administration-free interval.

It can thereby be provided that at least one of the hormonal components is orally administered.

The invention further provides that at least one of the hormonal components is transdermally administered.

It is also provided that at least some of the daily units of at least one of the hormonal components are administered as a sustained release unit.

Finally, it can be provided that the daily units of the second hormonal component or components include an estrogen content that is incrementally increasing.

It was surprisingly discovered that a high contraceptive reliability is achieved in the first cycle when an ovulation-inhibiting method of the type involving administration of the second hormonal component, i.e., of the estrogen/progestogen combination, is begun on the first day of menstruation. One can proceed likewise when switching to a highly dosed preparation of a conventional type of ovulation-inhibiting method of the type, i.e., immediate administration of the daily units of the second hormonal component following the last estrogen/progestogen tablet of the traditional preparation, even though this would not actually be necessary.

The method of the invention can be implemented upon employment of a standard packaging (for example, 7 daily units of the first hormonal component and 21 daily units of the second hormonal component) of the type in that the 7 daily units or, respectively, tablets of the first hormonal component are discarded in the first administration cycle, so that administration of the first daily unit of the second hormonal component is begun immediately on the first menstruation day. Administration according to the standard plan follows thereafter.

On the other hand, however, one can also proceed such that a packaging unit is employed wherein the second hormonal component is assigned to administration days 1–21, for a desired, overall cycle of 28 days, and the first hormonal component is assigned to administration days 22–28, whereupon the next packaging unit beginning with the second hormonal component then follows, etc.

A further alternative involves employing a packing unit wherein the numbers of the administration days can be set by the user, so that the first administration day falls either on the first daily unit of the first hormonal component or on the first daily unit of the second hormonal component, whereby a round packaging form can be potentially employed, for example, for the commercially-obtainable preparation "Trisequens".

The first hormonal component and the second hormonal component of the ovulation-inhibiting method of the invention, moreover, can be combined according to German Letters Patent 41 04 385, which is referenced for further explanation in this regard.

Regarding the possibility of transdermal administration of at least one of the hormonal components that is provided though not preferred in the invention, it should be noted that Brit. Med. J. 297 (1988), 900–901 has already disclosed that an ovulation inhibition be achieved by transdermal application of 200 µg estradiol daily, using patches that are changed every three days. The ovulation-inhibition occurs due to the effect of the permanently elevated estradiol level without a progestogen being administered. In order to avoid an endometrium hyperplasia, a progestogen can be additionally administered over 7–10 days in every cycle, although this does not significantly contribute to the endometrium stimulation due to the brevity of administration. The described method is less reliable for young women and, differing from the invention, does not prescribe the employment of a hormonal component wherein a progestogen preparation is present in a dosage that adequately inhibits ovulation.

Exemplary embodiments of the invention shall be set forth below.

EXAMPLE 1

For ovulation-inhibiting treatment, a sequential preparation was employed that contained 21 daily units, each having respectively 2 mg estradiol and 1 mg norethisterone acetate, as well as 7 daily units each having respectively 2 mg estradiol. The first daily unit, having 2 mg estradiol and 1 mg norethisterone acetate, was taken on the first day of menstruation given initial administration, whereupon the further daily units, each having respectively 2 mg estradiol and 1 mg norethisterone acetate and, following thereupon, the 7 daily units having respectively 2 mg estradiol each were administered, followed immediately by the first of the 21 daily units having respectively 2 mg estradiol and 1 mg norethisterone acetate, each contained in the package that follows: The treatment was administered over one year and exhibited practically no side effects from the very outset and resulted in extremely good contraceptive reliability.

EXAMPLE 2

An ovulation-inhibiting means was employed that contained 18 daily units each having, respectively, 20 µg ethinyl estradiol and 150 µg ethinyl gestradiol, as well as 10 daily units each having, respectively, 20 µg thinyl estradiol. Administration was identical to Example 1. The observations were identical to Example 1.

EXAMPLE 3

An intramuscular injection of 50 mg estradiol undecylate was taken every 4 weeks (on the first day, respectively) for ovulation-inhibition. Additionally, 2 mg cyproterone acetate were taken orally from day 6 through day 28 (23 daily units). The method exhibited practically no side effects with the achievement of desirable contraceptive reliability.

EXAMPLE 4

100 µg estradiol daily were applied transdermally, with the assistance of a patch that was changed twice weekly, for ovulation-inhibition, i.e., on day 1, day 4, day 8, day 11, etc., consistently every 3.5 days. Additionally, 150 µg desogestrel was administered respectively on a daily basis between day 8 and day 28 (21 daily units). No noteworthy side effects were observed and desirable contraceptive reliability was achieved.

It should be understood that various changes and modifications to the presently preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

I claim:

1. A method of hormonal contraception comprising the steps of:

sequentially administering a composition for the total number of days of a desired cycles beginning with the first day of menstruation that includes a first hormonal component and a second hormonal component, the first hormonal component composed of a plurality of daily hormone units including a therapeutically effective amount of an estrogen preparation to cause disturbance of the follicle stimulation, the second hormonal component composed of a plurality of daily hormone units including a therapeutically effective amount of an estrogen preparation and a progestogen preparation to inhibit ovulation, the estrogen preparation of the second hormonal component not being a combination of a biologically produced estrogen and a synthetic estrogen;

separately packaging the first hormonal component and the second hormonal component in a joint packaging unit in separate packages which are individually removable from the joint packaging unit, with the plurality of daily hormone units equaling the total number of days of the desired cycle;

providing the daily units of the first hormonal component in a plurality which is lower that the plurality of daily units of the second hormonal component; and arranging the plurality of daily units of the second hormonal component in the joint packaging unit to cause a first daily unit of the second hormonal component to be administered on the first day of menstruation and further to cause said plurality daily units of the second hormonal component to be taken before the plurality of daily units of the first hormonal component.

2. The method of claim 1 further comprising the step of providing 5 daily hormone units in the first hormonal component and 23 daily hormone units in the second hormonal component.

3. The method of claim 1 further comprising the step of providing 14 daily units in the first hormonal component and 14 daily units in the second hormonal component.

4. The method of claim 1 further comprising the step of administering a first daily hormone unit of the second hormonal component on the first day of the cycle.

5. The method of claim 1 further comprising the step of continuously numbering the plurality of daily hormone units of the first hormonal component and the plurality of daily hormone units of the second hormonal component according to the total number of administration days of the desired cycle.

6. The method of claim 5 further comprising the step of fixing the numbering of daily hormone units.

7. The method of claim 5 further comprising the step of varying the numbering of daily hormone units such that the first administration day can be optionally assigned to the first daily hormone unit of the first hormonal component or the first daily hormone unit of the second hormonal component.

8. The method of claim 1 further comprising the step of administering at least one of the hormonal components orally.

9. The method of claim 1 further comprising the step of administering at least one of the hormonal components transdermally.

10. The method of claim 1 further comprising the step of combining the plurality of daily hormone units of at least one of the hormonal components to form a sustained release unit.

11. The method of claim 1 further comprising the step of separately packaging in the joint packaging unit at least two pairs of the first hormonal component and the second hormonal component.

12. The method of claim 1 further comprising the step of including an incrementally increasing estrogen preparation in the daily units of the second hormonal component.

13. A joint packaging unit for the administration of a hormonal contraceptive, the joint packaging unit comprising:

a first hormonal component including a plurality of daily hormone units which contain a therapeutically effective amount of an estrogen preparation to cause disturbance of the follicle stimulation;

a second hormonal component including a plurality of daily hormone units which contain a therapeutically effective combination of an estrogen preparation and a progestogen preparation to inhibit ovulation, the estrogen preparation not including a combination of a biologically produced estrogen and a synthetic estrogen;

the plurality of daily hormone units of the first hormonal component and the plurality of daily hormone units of the second hormonal component equaling a total number of days of a desired cycle;

the first hormonal component and the second hormonal component being separately packaged in respective packages within the joint packaging unit, the separate packages being individually removable from the joint packaging unit;

the plurality of daily units of the second hormonal component being arranged in the joint packaging unit such that the plurality of daily units of the second hormonal component are available to be removed from the joint packaging unit before the plurality of daily units of the first hormonal component;

the plurality of daily units of the second hormonal component being further arranged so that a first daily unit of the second hormonal component is available to be removed on the first day of the menstruation; and the plurality of daily hormone units of the second hormonal component is less than the plurality of daily hormone units of the first hormonal component.

14. The joint packaging unit of claim 13 wherein the first hormonal component includes 5 daily hormone units and the second hormonal component includes 23 daily hormone units.

15. The joint packaging unit of claim 13 wherein the first hormonal component includes 14 daily hormone units and the second hormonal component includes 14 daily hormone units.

16. The joint packaging unit of claim 13 wherein a first daily hormone unit of the second hormonal component is administered on the first day of the desired cycle.

17. The joint packaging unit of claim 13 wherein the plurality of daily hormone units of the first hormonal component and plurality of daily hormone units of the second hormonal component are continuously numbered according to the total number of administration days of the desired cycle.

18. The joint packaging unit of claim 17 wherein the numbering of the daily hormone units is fixed.

19. The joint packaging unit of claim 17 wherein the numbering of daily hormone units is variable such that the first administration day can be optionally assigned to the first daily hormone unit of the first hormonal component or the first daily hormone unit of the second hormonal component.

20. The joint packaging unit of claim 13 wherein at least one of the hormonal components is for oral administration.

21. The joint packaging unit of claim 13 wherein at least one of the hormonal components is for transdermal administration.

22. The joint packaging unit of claim 13 further comprising a sustained release unit formed from combining the plurality of daily hormone units of at least one of the hormonal components.

23. The joint packaging unit of claim 13 wherein at least two pairs of the first hormonal component and the second hormonal component are separately packaged in the common packaging unit.

24. The joint packaging unit of claim 13 wherein the daily units of the plurality of daily units of the second hormonal component include an incrementally increasing estrogen preparation.

* * * * *